United States Patent [19]

Login et al.

[11] Patent Number: 4,883,655

[45] Date of Patent: Nov. 28, 1989

[54] QUATERNIZED NITROGEN CONTAINING POLYCYCLIC COMPOUNDS

[75] Inventors: Robert B. Login, Oakland; Ratan K. Chaudhuri, Butler; David J. Tracy, Lincoln Park; Michael W. Helioff, Westfield, all of N.J.

[73] Assignee: GAF Corporation, Wayne, N.J.

[21] Appl. No.: 91,010

[22] Filed: Aug. 28, 1987

Related U.S. Application Data

[63] Continuation-in-part of Ser. No. 922,923, Oct. 24, 1986, Pat. No. 4,732,900.

[51] Int. Cl.$^4$ .................. C07D 401/06; C07D 403/06; C07D 413/06; C07D 417/06

[52] U.S. Cl. ......................... 424/70; 424/47; 424/49; 424/53; 424/54; 424/73; 540/451; 540/470; 540/480; 540/542; 544/98; 544/141; 544/335; 544/372; 546/104; 546/146; 546/175; 546/208; 546/209; 546/281; 548/146; 548/180; 548/204; 548/208; 548/236; 548/247; 548/281; 548/336; 548/327; 548/364; 548/374; 548/440; 548/465; 548/480; 548/481; 548/524

[58] Field of Search ............... 540/451, 531, 524, 525, 540/480; 546/243, 208, 281, 175, 146, 104; 548/550, 524, 465, 440, 480, 481; 514/183, 212, 351, 424; 424/70, 71, 72, DIG. 3, DIG. 4, 62, 63, 64, 69, 47, 49, 53, 54, 73

[56] References Cited

U.S. PATENT DOCUMENTS

| | | | |
|---|---|---|---|
| 3,138,610 | 6/1964 | Buc et al. | 424/71 X |
| 4,189,468 | 2/1980 | Vanlerberghe | 424/71 X |
| 4,532,127 | 7/1985 | Feinland et al. | 424/62 |
| 4,590,069 | 5/1986 | Deckner et al. | 424/64 X |
| 4,608,250 | 8/1986 | Jacquet et al. | 424/72 X |
| 4,612,188 | 9/1986 | Zorayan et al. | 424/62 X |
| 4,710,374 | 12/1987 | Grollier et al. | 424/72 X |
| 4,732,990 | 3/1988 | Login et al. | 540/531 X |

FOREIGN PATENT DOCUMENTS 1326561  4/1963  France .................. 424/71

OTHER PUBLICATIONS

Noller, "Chemistry of Organic Compounds", 1965, 3rd Ed., p. 253.

Primary Examiner—Joseph P. Brust
Attorney, Agent, or Firm—Marilyn J. Maue; Joshua J. Ward

[57] ABSTRACT

The invention relates primarily to quaternized polycyclic compounds having the formula

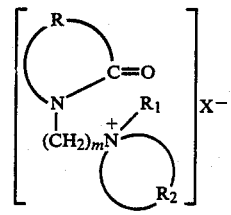

wherein m is an integer having a value of from 1 to 4; R is alkylene having from 3 to 8 carbon atoms and is optionally substituted with $C_1$ to $C_4$ alkyl; $R_2$ together with the quaternary nitrogen, forms a 5 to 14 membered heterocyclic ring, said ring containing from 1 to 2 hetero atoms selected from the group of nitrogen, sulfur and oxygen; $R_1$ forms a double bond in the heterocyclic ring of the quaternized nitrogen or is alkyl, alkyleneoxyalkyl, alkylhydroxy, aryl, aralkyl, aralkenyl, alkaryl, alkylamidoalkyl and $X^-$ is a chloride, bromide or iodide anion. The invention also relates to the preparation and use of said quaternized polycyclic compounds.

18 Claims, No Drawings

QUATERNIZED NITROGEN CONTAINING POLYCYCLIC COMPOUNDS

In one aspect the invention relates to novel quaternized polycyclic compounds which possess viscosity enhancing and hair conditioning properties, particularly in the presence of anionic surfactants. In another aspect the invention relates to novel quaternized polycyclic compounds having bactericidal properties. Still another aspect of the invention relates to the preparation of said quaternized polycyclic compounds and in still another aspect, the invention relates to the use of said compounds in several fields of application.

BACKGROUND OF THE INVENTION

The selection of components for hair and skin treating formulations presents numerous difficulties involving compatibility. Several hair treatment and shampoo formulations have been developed which aim to provide conditioning action during cleansing so as to leave the hair soft, manageable and lustrous and thus to eliminate a separate application of creme rinses or conditioning treatments. Problems arise from the limited compatibility of anionic detergents with commercial cationic conditioning agents which precipitate out of solution in shampoo formulations.

Shampoo formulations have employed conventional anionic surfactants such as sodium lauryl sulfate, ammonium lauryl sulfate, ammonium lauryl ether sulfate and sodium lauryl ether sulfates which have been found to be incompatible with most cationic conditioning at effective concentration levels.

Additionally, reproducible thickening formulations containing anionic detergents such as sodium α-olefin sulfonates is very difficult to achieve.

Still another problem encountered in hair conditioning shampoos is one of a preservative nature. It has been found that shampoos, containing inadequate preservative, on standing develop strands of *Pseudomonas aerouginosa* which are clearly visible in the liquid and which may cause scalp infection. Consequently, separate preservatives are added to the formulation to prevent development of this bacteria and prevent skin infection. These and many other problems are encountered in the formulation of various shampoos, conditioners and cream rinses. Certain of these difficulties are also encountered in skin lotions, healing salves, mouthwashes, etc.

Accordingly it is an object of this invention to minimize or obviate the above problems while providing additional benefits in hair and skin treating formulations.

Another object of the invention is to provide novel quaternized nitrogen containing compounds having unique properties.

Another object is to provide novel quaternized nitrogen containing compounds having excellent hair conditioning and thickening properties when incorporated into a shampoo and having high compatibility with components of hair and skin treating formulations.

Another object is to provide an economical and commercially feasible method for the preparation of said novel quaternized nitrogen containing compounds.

Still another object is to provide processes for the use of said quaternized compounds.

These and other objects will become apparent from the following description and disclosure.

THE INVENTION

According to this invention there is provided quaternized polycyclic compounds having unique properties and defined by the formula

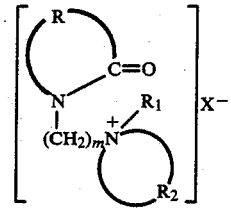

wherein $X^-$ is a chloride, bromide or iodide anion; m is an integer having a value of from 1 to 4; R is alkylene having from 3 to 8 carbon atoms and is optionally substituted with $C_1$ to $C_4$ alkyl; $R_1$ forms a double bond in the heterocyclic ring with the quaternized nitrogen or is alkyl, alkyleneoxyalkyl, alkylhydroxy, aryl, aralkyl, aralkenyl, alkaryl and alkylamidoalkyl, said groups containing up to 30 carbon atoms; and $R_2$ together with the quaternary nitrogen atom forms a 5 to 10 membered monocyclic ring, a 9 to 10 membered bicyclic ring or a 13 to 14 membered tricyclic ring, at least one of said rings containing from 1 to 2 hetero atoms selected from the group of nitrogen, sulfur and oxygen and being saturated or unsaturated as may occur for example in the rings of thiazirine, N-methyl-thiazine, N-methyloxazine, thiazepine, N-ethyl-oxazocine, diazocine, N-methylazonine, antipyrine, conyrine, coniine, collidine, diazine, imidazole, isoxazole, lutidine, N-methyl hexahydropyridine, morpholine, oxazole, picoline, piperidine, pyrine, pyrazole, pyridine, pyrrolidine, pyrrole, pyrroline, N-ethylbenzopyrrole, N,N'-dimethyl-dipyrrylmethane, decahydroquinoline, methyl indole, nicotine, quinoline, quinaldine, acridine and carbazole. As indicated, a heterocyclic ring of the $R_2$ moiety may contain carbonyl substitution or the ring itself can be substituted with a lower alkyl, amino or amido group.

Preferred compounds within the above group are those wherein m is 1; R is —$CH_2$—$CH_2$—$CH_2$—; $R_1$ is a double bond or a group having $C_8$ to $C_{22}$ carbon atoms, most preferably alkyl and $X^-$ is a chloride anion. The most preferred compounds of this group are those wherein $R_2$ together with the quaternized nitrogen forms a oxazolidinyl, pyrrolidinyl, piperidinyl, morpholinyl, pyridinyl or imidazolinyl ring. Examples of the present polycyclic compounds include:

N-hexadecyl-N-[(2-pyrrolidonyl)methyl] pyrrolium chloride

N-octadecyl-N-[(2-pyrrolidonyl)methyl] pyrrolidinium chloride 2-ethyl-N-[(2-piperidonyl)methyl] 2-oxazolinium chloride N-octadecyl-N-[(2-pyrrolidonyl)methyl] oxazolidinium chloride 5-methyl-N-[(2-pyrrolidonyl)methyl] isooxazolium chloride N-ethyl-N-[(2-piperidonyl)methyl] isooxazolidinium chloride 2-methyl-N-[(2-pyrrolidonyl)methyl] thiazolinium chloride N-dodecyl-N-[(2-pyrrolidonyl)methyl] thiazolidinium chloride 1-(2-hydroxyethyl)-2-heptadecyl-1(or 3)-[(2-pyrrolidonyl)methyl]-2-imidazolinium chloride
1-(2-hydroxyethyl)-2-pentadecyl-1(or 3)-[(2-pyrrolidonyl)methyl]-2-imidazolinium chloride
1-(2-hydroxyethyl)-2-heneicosyl-1(or 3)-[(2-pyrrolidonyl)methyl]-2-imidazolinium chloride
1-(2-hydroxyethyl)-2-tridecyl-1(or 3)-[(2-pyrrolidonyl)-methyl]-2-imidazolinium chloride
1-methyl-2-dodecyl-1(or 3)-[(2-pyrrolidonyl)methyl]-2-imidazolinium chloride
4-hexadecyl-N-[(2-pyrrolidonyl)methyl] pyridinium chloride
N-octadecyl-N-[(2-pyrrolidonyl)methyl] piperidi chloride
1,4-diethyl-1(or 4)-[(2-pyrrolidonyl)methyl] piperazinium chloride
2-methyl-1(or 3)-[(2-pyrrolidonyl)methyl] pyrimidinium chloride
N-octadecyl-N-[(2-pyrrolidonyl)methyl] morpholinium chloride
N-octadecyl-N-[(2-azacycloheptanonoyl)methyl] morpholinium chloride
4-ethyl-N-[(2-pyrrolidonyl)methyl] quinolinium chloride
4-methyl-N-[(2-pyrrolidonyl)methyl] tetrahydroquinolinium chloride
4-ethyl-N-[(2-pyrrolidonyl)methyl] isoquinolinium chloride
4-ethyl-N-[(2-pyrrolidonyl)methyl] tetranydroisoquinolinium chloride
N-methyl-N-[(2-pyrrolidonyl)methyl] benzisooxazolinium chloride
N-ethyl-N-[(2-pyrrolidonyl)methyl] benzthiazolinium chloride
N-octadecyl-N-[(2-pyrrolidonyl)methyl] indolinium chloride
N-dodecyl-N-[(2-pyrrolidonyl)methyl] indolinium chloride
2-hexyl-N-[(2-pyrrolidonyl)methyl] benzimidazolinium chloride
N-ethyl-N-[(2-pyrrolidonyl)methyl] acridinium chloride
N-methyl-N-[(2-pyrrolidonyl)methyl]-9-acridinium chloride
N-octadecyl-N-[(2-pyrrolidonyl)methyl] carbazolinium chloride
N-[(2-pyrrolidonyl)methyl] thiazepinium chloride
N-methyl-N-[(2-pyrrolidonyl)methyl] thiazinium chloride
N-[(2-pyrrolidonyl)methyl] antipyrinium chloride
N-[(2-pyrrolidonyl)methyl] diazinium chloride
N-propyl-N-[4-(2-pyrrolidonyl)butyl] pyrazolinium chloride
N-dodecyl-N-[2-(2-pyrrolidonyl)ethyl] pyrrolinium chloride 1,2-bis-[2-(2-pyrrolidonyl)ethyl] antipyrinium chloride
N,N'-bis-[(2-pyrrolidonyl)methyl] nicotinium chloride
methylene-bis- N-methyl-N-[(2-pyrrolidonyl)methyl] pyrrolium chloride
N,N'-dimethyl-N,N'-bis-[(2-pyrrolidonyl)methyl] diazacyclohendacanium chloride
N,N'-diethyl-N,N'-bis-[(2-pyrrolidonyl)methyl] diazacyclotetradecanium chloride
and other lower alkyl substituted species of quaternized halides of N-haloalkyl 2-pyrrolidones, 2-piperidones, 2-azacycloheptanones, 2-azacyclooctanones, 2-azacyclononanones, and 2-azacyclododecanones More specifically, the products of this invention can be described by the formula:

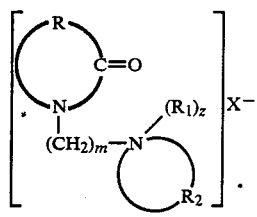

wherein z has a value of zero when the quaternized nitrogen atom is bonded in the heterocyclic ring by a double bond and a single bond and has a value of one when the quaternized nitrogen atom is bonded in the heterocyclic ring by two single bonds. All of the remaining definitions of R, $R_2$, $R_1$ and m being the same as set forth above.

The present quaternary compounds possess unique properties among which is their ability to build viscosity, e.g. for liquids having a viscosity less than 50 centipoises, while simultaneously providing a hair and skin conditioning capability in cosmetic formulations containing anionic surfactants. They are also useful in textile treating formulations to provide a softer, silky texture. For the purposes of this invention, the term "conditioning" is intended to include the functions of moisturizing, softening, cleansing, penetrating, luster enhancing, hair combability, dye leveling, dye retention and others. These compounds are highly compatible with α-olefin sulfonates and anionic surfactant salts conventionally employed in shampoos, skin lotions and like formulations. Their compatibility is such that up to 5% by weight or more of the quaternized compounds can be incorporated in a composition, a characteristic which permits the formation of effective formulations as liquids or gels. In contrast, most prior quaternary viscosity building conditioning compounds are incorporatable only up to 0.5 or 1 wt. percent based on total anionic content. The pyrrolidonyl compounds are particularly outstanding for their compatability, viscosity building and conditioning properties. These compounds are also outstanding for their biocidal properties and can be used in a mouthwash or as a highly compatable preservative in shampoo, hair conditioners and hand or body lotions. It is contemplated that mixtures of the pyrrolidonyl compound can be employed in shampoos, hair conditioners and lotions as an agent which incorporates thickening, conditioning and preservative qualities in one additive; thus eliminating the need for separate chemical components to accomplish these individual needs. These mixtures and particularly the sulfur-containing quaternized products, may also be used to control dandruff or bacterial infections of the scalp and body skin. Generally, the quaternary compounds of this invention are mixed with a standard formulation of shampoo, cream rinse, hand or body lotion or creams, mouthwash, etc., in an effective amount which ranges from between about 0.05 to about 8% by weight, preferably between about 0.5 and about 5% by weight, of the total formulation. The compatability of the present compounds with anionic α-olefin sulfonates is surprising since most anionic compounds cause precipitation of cationic agents. However, the present compounds in concentrations up to 5% by weight show no tendency to precipitate after extended periods including periods up to 6 months or more.

The quaternary pyrrolidonyl compounds of this invention are prepared by an economically feasible process which involves the reaction between the corresponding heterocyclic amine and a N-haloalkyl lactam having a 5 to 10 membered ring. A general equation for the preparation is defined by the equation:

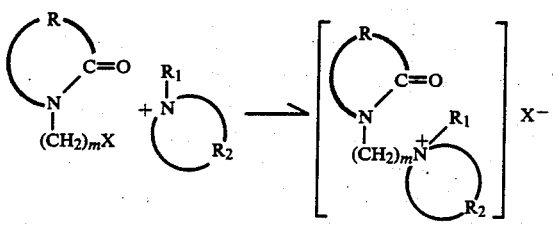

wherein m, R, $R_1$, $R_2$ and $X^-$ are as defined above and X is chloro, bromo or iodo.

Examples of suitable lactam reactants include the N-chloromethyl, N-bromomethyl and N-iodomethyl derivatives of 2-pyrrolidone, 4-methyl-2-pyrrolidone, 4-butyl-2-pyrrolidone, 2-piperidone, methyl-2-piperidone, 2-azacycloheptanone, 2-azacyclooctanone, 2-azacyclononanone, 2-azacyclodecanone and $C_1$ to $C_4$ alkyl derivatives substituted on an alkylene group in the heterocyclic ring of these lactams. Mixtures of these lactam reactants can also be employed to provide a correspondingly mixed quaternary product, if desired. Of these lactam reactants the N-halomethyl-2-pyrrolidones and N-halomethyl caprolactams are preferred and the N-chloromethyl lactams are most preferred.

Suitable nitrogen heterocyclic amino coreactants include any of the compounds defined by the aforementioned $R_2$—N—$R_1$ heterocyclic group. Preferred of this group are pyridine, oxazolidine and N-alkyl substituted pyrrolidines, piperidines, morpholines and imidazoles wherein most preferably the alkyl bonded to the heterocyclic nitrogen contains from 8 to 20 carbon atoms. Also, the most preferred heterocyclic amine coreactants of this invention are those wherein $R_2$ is a hydrocarbon group having a total of 4 or 5 carbon atoms.

The process is effected by reacting the haloalkyl lactam and the nitrogen heterocyclic amine coreactant at a temperature between about 25° and about 120° C., preferably between about 60° and about 100° C., under a pressure of from about 0 to about 50 psig, preferably atmospheric pressure, for a period up to about 10 hours, usually not more than 5 hours is required to complete the reaction. From the above equation, it is seen that stoichiometric amounts of haloalkyl lactam and amine are used in the reaction. However, an excess of one or the other of the components is practicible in the process. Generally, for economic considerations, and where the coreactant contains a single quaternizable site, a mole ratio of between 1:1.5 and about 1.5:1 is employed; although, a slight excess of the tertiary amino coreactant to insure complete reaction of the lactam is recommended. Accordingly, the most preferred mole ratio of lactam to amine is about 1:1.01–1:1.03.

It is to be understood, however, that in instances where more than one quaternizable site is present in the coreactant, the molar amount of the haloalkyl lactam can be increased accordingly.

It is also recommended that the haloalkyl lactam be added gradually or dropwise to the amine at the beginning of the ensuing exothermic reaction. At the completion of the reaction, a solid product is formed and recovered. Since the reaction is quantitative, the product can be used as is or, when a slight excess of the amine is employed, it can be neutralized with a weak acid such as acetic, lactic or citric acid.

For incorporating into a standard formulation of shampoo, cream rinse, hand or body lotion, etc., the present product is dissolved in an inert solvent such as water, propylene glycol, ethanol, etc., and the solution in the desired amount is mixed into the formulation to provide a homogeneous liquid, gel, cream or lotion. Incorporation of the present product is usually affected at room temperature under atmospheric pressure and requires no special formulating technique. However, for certain formulations incorporation of the present product can be effected at temperatures up to about 85° C. Amphoteric-containing shampoo formulations are best prepared by initially preparing an aqueous solution of the quaternized product and the amphoteric surfactant and then adding the solution to the shampoo formulation.

Having generally described the invention, reference is now had to the accompanying examples which set forth preferred embodiments, but which are not to be construed as limiting to the scope of the invention as more broadly set forth above and in the appended claims.

EXAMPLE I

To a 1 liter, 4-neck flask equipped with mechanical stirrer, reflux condenser, thermometer, and dropping funnel was added pyridine (0.505 mole) which was heated with stirring to 70° C. under $N_2$ blanket after which the heating source was removed and N-chloromethyl-2-pyrrolidone (0.5 mole) was added to the amine dropwise over a period of 25 minutes. An exothermic reaction ensued and was controlled at 100° C. by the rate of addition of N-chloromethyl-2-pyrrolidone. The reaction mixture changed from a liquid to a paste during the addition of N-chloromethyl-2-pyrrolidone and finally to a solid (powder) on completion of the reaction. The yield of N-[(2-pyrrolidonyl)methyl] pyridinium chloride, m.p. 160°–162° C., was quantitative. The content of the quaternary compound was determined by titration. (Mercuric Acetate method as described by Sidney Siggia, "Quantitative Organic Analysis via Functional Group", 1963, 3d Ed., John Wiley & Sons, pages 552–554).

EXAMPLE II

The reaction of Example I was repeated except that the amine used was N-methyl-morpholine (2% molar excess with respect to N-chloromethyl-2-pyrrolidone). The product, N-ethyl-N-[(2-pyrrolidonyl)methyl] morpholinium chloride was recovered as a paste in quantitative yield.

EXAMPLE III

The process of Example I was repeated except that the amine used was 3-octadecyl oxazolidine. The yield of N-octadecyl-N-[(2-pyrrolidonyl)methyl] oxazolidinium chloride is quantitative.

EXAMPLE IV

The process of Example I was repeated except that the amine used was 5-methyl-isoxazolidine. The yield of N-hexadecyl-5-methyl-N-[(2-pyrrolidonyl)methyl] oxazolidinium chloride is essentially quantitative.

EXAMPLE V

The process of Example I was repeated except that the amine used was 1-(2-hydroxyethyl)-2heptadecyl-2-imidazoline. The yield of 1-(2-hydroxyethyl)-2-heptadecyl-1(or 3)-[(2-pyrrolidonyl)methyl] 2-imidazolinium chloride is quantitative.

EXAMPLE VI

The process of Example I was repeated except that the amine used was 1-(2-hydroxyethyl)-2-undecyl imidazoline. The yield of 1-(2-hydroxyethyl)-2-undecyl-1(or 3)-[(2-pyrrolidonyl)methyl] imidazolinium chloride is quantitative.

EXAMPLE VII

The process of Example I was repeated except that the amine used was 3-hexadecyl-pyridine. The yield of 3-hexadecyl-N-[(2-pyrrolidonyl)methyl] pyridinium chloride.

EXAMPLE VIII

The process of Example I was repeated except that the amine used was N-octadecyl-piperidine. The yield of N-octadecyl-N-[(2-pyrrolidonyl)methyl] piperidinium chloride is quantitative.

EXAMPLE IX

The process of Example I was repeated except that the amine used was N-octadecyl-morpholine. The yield of N-octadecyl-N-[(2-pyrrolidonyl)methyl] morpholinium chloride is quantitative.

EXAMPLE X

The process of Example IX was repeated except that N-chloromethyl caprolactam was used instead of N-chloromethyl-2-pyrrolidone. The yield of N-octadecyl-N-[(2-azacycloheptanonyl)methyl] morpholinium chloride is quantitative.

EXAMPLE XI

The process of Example I was repeated except that the amine used was N-dodecyl-indoline. The yield of N-dodecyl-N-[(2-pyrrolidonyl)methyl] indolinium chloride is quantitative.

EXAMPLE XII

The process of Example I is repeated except that N-octadecyl thiazine is substituted for pyridine. The yield of N-octadecyl-N-[(2-pyrrolidonyl)methyl] thiazinium chloride is quantitative.

EXAMPLE XIII

The process of Example I is repeated except that N,N'-diethyl diazacyclotetradecane is substituted for pyridine and the amount of N-chloromethyl-2-pyrrolidone reactant is doubled. The yield of N,N'-diethyl-N-N'-bis-[(2-pyrrolidonyl)methyl] diazacyclotetradicanium chloride product is quantitative.

EXAMPLE XIX

Although all of the present quaternized compounds possess excellent surfactant properties, certain members are particularly recommended for incorporation into specific types of cosmetic formulations. Table III lists some of such uses for individual quaternized products within the scope of this invention, together with a brief description of the benefits derived from their incorporation.

Generally, the present products are added to the formulations in amounts between about 0.1 and about 5 wt. %, based on active ingredients. The quaternized compounds in Table I have the general formula:

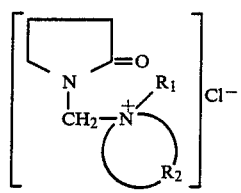

TABLE I

| No. | Compound where $R_2$ is/$R_1$ is | For Formulation In | Benefits Achieved |
|---|---|---|---|
| 1 | —(CH$_2$)$_7$—/ —C$_2$H$_4$OH | cream rinse | improved wet/dry combing-luster-softness |
| 2 | —(CH$_2$)$_4$—/ —C$_6$H$_4$—C$_8$H$_{17}$ | hair conditioner | improved wet/dry combing overall conditioning & increased luster & shine |
| 3 | CH$_3$—, CH$_3$—N, =O  /—C$_6$H$_5$ (derived from antipyrine) | blow-dry styling & moisturizing lotion | protection from heat-increased luster, shine body & overall conditioning |
| 4 | H$_{25}$C$_{12}$—⟨ring⟩—/—CH$_3$ (derived from 3-dodecyl piperidine) | bubble bath & textile softener | high compatability, smooth hand & viscosity enhancement |

TABLE I-continued

| No. | Compound where R₂ is/R₁ is | For Formulation In | Benefits Achieved |
|---|---|---|---|
| 5 | 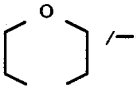 /—C$_{18}$H$_{37}$<br>(derived from N—octadecyl morpholine) | syndet bar & after-sun lotion | improved moisturizing-high compatibility & easy rubb-in |
| 6 |  /—C$_{14}$H$_{29}$<br>(deriverd from N—tetradecyl imidazole) | non-alcoholic mousse | conditioning-increased body, luster & shine |
| 7 | 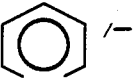 /—*<br>(derived from pyridine) | aerosol shave creams | high compatability-improved spreadability skin smoothing |
| 8 |  /—C$_{12}$H$_{25}$<br>(derived from N—dodecyl indole) | mousse hand & body lotion | improved rubb-in & smoother after-feel |
| 9 |  /—C$_{16}$H$_{33}$<br>(derived from N—hexadecyl carbazole) | moisturizing lotion | high compatability-good skin substantivity and penetration |
| 10 | 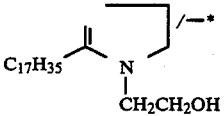 /—*<br>(derived from N—hydroxyethyl-2-heptadecyl imidazoline) | hair conditioner | improved combability, luster & shine |
| 11 | —CH=CH—O—CH=CH—/ —C$_{12}$H$_{25}$<br>(derived from N—dodecyl oxazine) | conditioning shampoo | overall conditioning & cleaning- compatability with anionic components-viscosity enhancing |
| 12 | —(CH$_2$)$_9$—/ —C$_6$H$_4$(CH$_3$) | oily hair shampoo | greaseless conditioning-viscosity building-improved wet/dry combability |
| 13 | —(CH$_2$)$_4$—/ —C$_6$H$_3$(CH$_3$)$_2$ | hair mist conditioner | improved wet/dry combing, luster & shine |
| 14 | 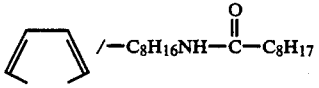 /—C$_8$H$_{16}$NH—C(=O)—C$_8$H$_{17}$<br>(derived from N—octylamido-octyl pyrole) | hair hot oil treating lotion | improved conditioning, luster, shine, wet/dry combability & body |
| 15 | 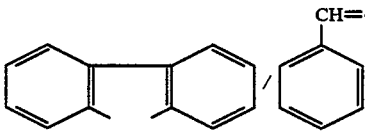<br>(derived from N—styryl carbazole) | after-shave lotion | easy rubb-in, skin conditioning & lasting effect |

TABLE I-continued

| No. | Compound where $R_2$ is/$R_1$ is | For Formulation In | Benefits Achieved |
|---|---|---|---|
| 16 | 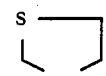 /—$C_{16}H_{33}$<br>(derived from N—hexadecyl-thiazolidine) | dandruff shampoo & skin medicant | good antibacterial and fungicidal properties |
| 17 | 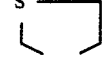 /—$C_{12}H_{25}$<br>(derived from N—dodecyl-thiazolidine) | dandruff shampoo & skin medicant | good antibacterial and fungicidal properties |
| 18 | —$(CH_2)_4$—NH—$(CH_2)_4$—$CH_2$—/<br>—$C_{12}H_{25}$<br>(derived from N—dodecyl diazacyclohendecane) | hair shampoo conditioner & setting lotion | improved moisturizing for damaged hair |

*forms a double bond in the heterocyclic ring

Examples of specific formulations for the above uses achieving the benefits noted are presented as follows.

EXAMPLE XX

CREAM RINSE

| Ingredients | Parts by Weight |
|---|---|
| Compound No. 1 in Table I | 2.0 |
| cetyl alcohol | 2.0 |
| emulsifying wax | 2.0 |
| citric acid | to pH 4 |
| deionized water | qs |
| fragrance | qs |
| preservative | qs |

HAIR CONDITIONER

| Ingredients | Parts by Weight |
|---|---|
| Compound No. 2 in Table I | 4.0 |
| PEG-8 Distearate | 2.5 |
| mineral oil | 1.5 |
| lanolin alcohol | 1.0 |
| stearic acid | 1.0 |
| PPG-20 methyl glucose ether | 1.0 |
| hydrolized animal protein | 0.25 |
| citric acid | to pH 4 |
| deionized water | qs |
| preservative | qs |
| fragrance | qs |

BLOW DRY STYLING LOTION

| Ingredients | Parts by Weight |
|---|---|
| Compound No. 3 in Table I | 1.5 |
| ethanol | 3.0 |
| polyquaternium* 11 | 2.0 |
| PEG-10 Castor oil | 0.2 |
| fragrance | 0.2 |
| phosphoric acid | to pH 6 |
| deionized water | qs |

CONDITIONING HAIR SPRAY

| Ingredients | Parts by Weight |
|---|---|
| Compound No. 15 in Table 1 | 0.6 |
| ethanol | 75.0 |
| ethyl ester of PVM/MA** copolymer | 4.1 |
| 2-amino-2-methyl-1-propanol 99% | 0.1 |
| fragrance | 0.2 |
| propellant | 20.0 |

*the quaternized ammonium polymer formed by reacting dimethyl sulfate and a copolymer of vinyl pyrrolidone and dimethylamino methylacrylate
**vinyl methyl ether/maleic anhydride

CONDITIONING SHAMPOO

| Ingredients | Parts by Weight |
|---|---|
| Compound 11 in Table I | 3.0 |
| N—dodecyl-2-pyrrolidone | 0.6 |
| polyquaternium 11 | 0.5 |
| sodium laureth-4-phosphate | 0.8 |
| ammonium lauryl sulfate | 40.0 |
| silk protein | 0.25 |
| tetrasodium ethylenediamine tetra-acetic acid | 0.2 |
| deionized water | qs |
| colorant | qs |
| fragrance | qs |

MOISTURIZING LOTION

| Ingredients | Parts by Weight |
|---|---|
| Compound No. 9 in Table I | 2.0 |
| mineral oil 70 CTS | 2.0 |
| stearic acid | 3.0 |
| emulsifying wax | 3.0 |
| Dimethicone* 200 CTS | 1.5 |
| Carbomer 934** | 0.15 |
| Oleth-20*** | 1.0 |
| triethanolamine 98% | 1.0 |
| deionized water | qs |
| preservative | qs |
| fragrance | qs |

*a mixture of methylated siloxane polymers end-blocked with trimethyl siloxy units (dimethylpolysiloxane)
**cross-linked polymer of acrylic acid
***PEG ether of oleyl alcohol

BUBBLE BATH

| Ingredients | Parts by Weight |
|---|---|
| Compound No. 4 in Table I | 3.0 |
| ammonium nonoynol-4-sulfate | 30.0 |
| sodium cocoyl isothionate | 10.0 |
| cocamidopropyl hydroxysultaine | 10.0 |
| cocamide diethanolamide | 6.0 |
| sodium methyl cocyl taurate | 20.0 |
| aloe vera gel | 1.0 |
| coconut oil | 1.0 |
| glycol stearate | 1.0 |
| deionized water | qs |
| preservative | qs |
| colorant | qs |

SHAMPOO FOR OILY HAIR

| Ingredients | Parts by Weight |
|---|---|
| Compound No. 12 in Table I | 3.0 |
| N—dodecyl-2-pyrrolidone | 1.0 |
| tetrasodium ethylenediamine tetra-acetic acid | 0.2 |
| sodium lauryl sulfate | 20.0 |
| alpha-olefin sulfonate | 20.0 |

| -continued | |
|---|---|
| polyquaternium 11 | 0.5 |
| deionized water | qs |
| preservative | qs |
| colorant | qs |
| fragrance | qs |
| added inorganic salts as desired for viscosity modification | |

| MOUTHWASH | |
|---|---|
| Ingredients | Parts by Weight |
| Compound No. 6 in Table I | 0.05 |
| alcohol, 190° | 20.00 |
| thymol | 0.03 |
| glycerine | 10.00 |
| flavor | 2.0 |
| distilled water | qs |
| polysorbate 80 | 2.00 |

| SYNDET BAR (Superfatted) | |
|---|---|
| Ingredients | Parts by Weight |
| Compound No. 5 in Table I | 0.5 |
| stearic acid, triple pressed | 32.00 |
| kettle soap | 9.80 |
| sodium cocoyl isethionate | 49.00 |
| sodium methyl cocoyl taurate | 6.90 |
| citric acid, 50% aqueous | 0.60 |
| titanium dioxide | 0.20 |
| fragrance | 1.00 |

| WATER RESISTANT EMOLLIENT AFTER SUN LOTION | |
|---|---|
| Ingredients | Parts by Weight |
| Compound No. 8 in Table I | 3.0 |
| mink Oil, Light Fraction | 11.00 |
| glyceryl stearate, self emulsifying | 1.00 |
| stearic acid | 2.50 |
| mineral oil and lanolin alcohol | 2.00 |
| myristyl myristate | 3.000 |
| mineral oil | 10.00 |
| PVP/Eicosene copolymer | 2.00 |
| triethanolamine | 0.70 |
| sorbitol | 3.00 |
| hydroxyethylcellulose | 0.30 |
| distilled water | qs |
| preservative | qs |
| fragrance | qs |

| NON-ALCOHOLIC CONDITIONING MOUSSE | |
|---|---|
| Ingredients | Parts by Weight |
| Compound No. 6 in Table I | 5.00 |
| PVP K-30 | 2.00 |
| Oleth-20 | 0.50 |
| fragrance | qs |
| deionized water | 77.50 |
| propellant A-46 | 15.00 |

| SELF-HEATING AEROSOL SHAVING CREAM | |
|---|---|
| Employed dual dispensing valve for metering oxidant from $H_2O_2$ container and reductant from aerosol can. | |
| Ingredients | Parts by Weight |
| Compound No. 7 in Table I | 2.00 |
| stripped coconut fatty acid | 1.10 |
| sorbitol | 10.00 |
| stearic acid | 4.20 |
| PEG-40 soritan peroleate | 2.00 |
| triethanolamine | 3.00 |
| potassium hydroxide | 1.00 |
| potassium sulfite | 9.00 |
| fragrance | 0.80 |
| butyrated hydroxy toluene (BHT) | 0.01 |
| butyrated hydroxy anisole (BHA) | 0.01 |
| deionized water | qs |
| propellant | qs |

| HAIR MIST CONDITIONER (w/o added preservative) | |
|---|---|
| Ingredients | Parts by Weight |
| 50/50 Mixture No. 9 & 10 in Table I | 1.00 |
| propylene glycol dicaprylate/dicaprate copolymer | 0.30 |
| oleamidopropyl dimethylamine | 0.50 |
| deionized water | 98.2 |

| CATIONIC MOUSSE HAND/BODY LOTION | |
|---|---|
| (Used 85 Parts of the following formula to 15 parts propellant A-46) | |
| Ingredients | Parts by Weight |
| Compound No. 8 in Table I | 0.50 |
| acetylated polyoxyethylene lanolin | 2.00 |
| ethoxylated lanolin alcohols | 1.00 |
| glyceryl stearate, self-emulsifying | 5.50 |
| cetyl alcohol | 1.50 |
| mineral oil, 70 CTS | 1.50 |
| stearyl alcohol | 1.50 |
| glycerin | 3.00 |
| isopropyl myristate | 4.00 |
| dimethicone, 100 CTS | 2.00 |
| water | qs |
| preservative | qs |
| fragrance | qs |

| HOT OIL TREATMENT - (w/o added preservative) | |
|---|---|
| Ingredients | Parts by Weight |
| 50/50 mixture No. 4 & 14 in Table I | 1.50 |
| oleamidopropyl dimethyl amine | 1.00 |
| polyethylene glycol 6000 distearate | 2.00 |
| hexylene glycol | 4.00 |
| lactic acid, 88% | to pH 4.4 |
| color | qs |
| deionized water | qs |

| AFTER SHAVE BALM | |
|---|---|
| Ingredients | Parts by Weight |
| 50/50 mixture No. 16 & 17 in Table I | 1.00 |
| Carbomer 941 | 0.20 |
| tetasodium ethylene diamine tetra-acetic acid | 0.10 |
| cetearyl alcohol* and polyethylene glycol ether of cetearyl alcohol | 2.50 |
| isopropyl myristate | 1.00 |
| Oleth-20 | 1.00 |
| methyl gluceth 20 | 2.00 |
| triethanolamine, 98% | 0.20 |
| propylene glycol | 3.00 |
| SDA denatured alcohol | 7.50 |
| PVP/dimethylaminoethyl methacrylate | 7.00 |
| fragrance | 1.00 |
| distilled water | qs |

| DANDRUFF SHAMPOO AND SKIN MEDICANT | |
|---|---|
| Ingredients | Parts by Weight |
| Compound No. 16 in Table I | 4.2% |
| Sodium lauroyl sarcosinate, 30% | 10.0 |
| TEA lauryl sulfate, 40% | 25.0 |
| Magnesium aluminium silicate | 1.0 |
| Hydroxymethyl cellulose, E 4000 | 1.25 |
| Water, perfume, color (D & C Green #5) | qs |

*50/50 mixture of cetyl and stearyl alcohols

The above examples are representative or preferred embodiments of the present invention; however, it will be understood that other species of instant quaternized lactams can be substituted in the above formulations to provide the benefits indicated. Also, in the preparation of the quaternized lactams described in Examples I-XX, other lactam and/or heterocyclic amine reactants described herein can be substituted to provide the corresponding quaternized products which are also included within the scope of this invention. Particularly recommended among these substituted species are the halomethyl-2-caprolactam reactants and the amidoalkyl-substituted or hydroxy-substituted heterocyclic amine reactants having from 3 to 8 carbon atoms which also provide useful bactericidal and viscosity enhancing properties.

What is claimed is:

1. The quaternized compound having the formula

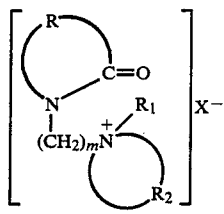

wherein $X^-$ is a chloride, bromide or iodide anion; m is an integer having a value of from 1 to 4; R is linear alkylene having from 3 to 8 carbon atoms and is optionally substituted with $C_1$ to $C_4$ alkyl; $R_1$ forms a double bond in the heterocyclic ring with the quaternized nitrogen or is selected from the group consisting of alkyl, hydroxyalkyl, alkyleneoxyalkyl, aryl, alkaryl, aralkyl, aralkenyl and alkylene amidoalkyl and $R_2$, together with the quaternary nitrogen atom forms a 5 to 14 membered heterocyclic structure optionally substituted with alkyl and having a single heteroatom.

2. The compound of claim 1 wherein R is alkylene having up to 4 carbon atoms and is optionally substituted with lower alkyl.

3. The compound of claim 1 wherein $R_2$ forms a saturated heterocyclic ring with the quaternized nitrogen and wherein $R_1$ contains from 8 to 22 carbon atoms.

4. The compound of claim 3 wherein $R_2$ forms a pyrrolidinyl ring.

5. The compound of claim 3 wherein $R_2$ forms a piperidinyl ring.

6. The compound of claim 1 wherein the heterocyclic ring formed between $R_2$ and the quaternized nitrogen atom contains a double bond and $R_1$ represents a double bond in said ring or is a group bonded to the quaternized nitrogen atom and contains from 8 to 22 carbon atoms.

7. The compound of claim 6 wherein $R_2$ forms a pyridinyl ring and $R_1$ represents a double bond within said ring.

8. The compound of claim 1 wherein $R_2$ together with the quaternized nitrogen atom forms a 5 to 10 membered heteromonocyclic ring.

9. The compound of claim 1 wherein $R_2$ together with the quaternized nitrogen atom forms a 9 to 10 membered heterobicyclic ring.

10. The compound of claim 1 wherein $R_2$ together with the quaternized nitrogen atom forms a 13 to 14 membered heterotricyclic ring.

11. The process of adding an effective hair or skin conditioning amount of the compound of claim 1 to a cosmetic formulation.

12. The process of claim 11 wherein the cosmetic formulation is a shampoo.

13. The process of adding an effective antibacterial amount of the compound of claim 1 to a liquid subject to bacterial degradation.

14. The process of applying an effective antibacterial amount of the compound of claim 1 to the skin or hair.

15. The process of contacting a fiber with an effective fiber softening amount of the compound of claim 1.

16. The process of adding an effective viscosity building amount of the compound of claim 1 to a liquid having a low viscosity to form a cream or gel.

17. The process of claim 11 wherein said cosmetic formulation contains an anionic component.

18. The process of claim 11 wherein said cosmetic formulation is a hair or skin conditioning formulation.

* * * * *